US009897561B2

(12) United States Patent
Isakov et al.

(10) Patent No.: US 9,897,561 B2
(45) Date of Patent: Feb. 20, 2018

(54) METHOD OF DETECTING DEFECTS IN AN OBJECT BASED ON ACTIVE THERMOGRAPHY AND A SYSTEM THEREOF

(71) Applicant: Agency for Science, Technology and Research, Singapore (SG)

(72) Inventors: Dmitry Isakov, Singapore (SG); Khee Aik Christopher Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 378 days.

(21) Appl. No.: 14/645,636

(22) Filed: Mar. 12, 2015

(65) Prior Publication Data
US 2015/0260667 A1    Sep. 17, 2015

(30) Foreign Application Priority Data

Mar. 12, 2014  (SG) .......................... 10201400586U (51) Int. Cl.
*G01N 25/72* (2006.01)
(52) U.S. Cl.
CPC .................... *G01N 25/72* (2013.01)
(58) Field of Classification Search
CPC ...................................................... G01N 25/72
See application file for complete search history.

(56) References Cited

U.S. PATENT DOCUMENTS

| 4,634,291 | A | 1/1987 | Bantel et al. |
| 5,711,603 | A | 1/1998 | Ringermacher et al. |
| 6,516,084 | B2 | 2/2003 | Shepard |
| 6,838,670 | B2 | 1/2005 | Lewis et al. |
| 7,044,634 | B2 | 5/2006 | Sandvoss |
| 7,220,966 | B2 | 5/2007 | Saito et al. |
| 2003/0193987 | A1* | 10/2003 | Zalameda ................. G01J 5/62 374/5 |
| 2005/0008215 | A1* | 1/2005 | Shepard ................. G01N 25/72 382/141 |

(Continued)

FOREIGN PATENT DOCUMENTS

| WO | 9940417 A1 | 8/1999 |
| WO | 2004063736 A1 | 7/2004 |

OTHER PUBLICATIONS

Wrobel et al., "The Application of Transient Thermography for the Thermal Characterisation of Carbon Fibre/Epoxy Composites," vol. 36, Issue 1, Journal of Achievements in Materials and Manufacturing Engineering, Sep. 2009, pp. 49-56.

(Continued)

*Primary Examiner* — Lisa Caputo
*Assistant Examiner* — Nasir U Ahmed
(74) *Attorney, Agent, or Firm* — Winstead, P.C.

(57) ABSTRACT

There is provided a method of detecting defects in an object based on active thermography, the method including heating a surface of the object at a plurality of localized regions thereof, selecting at least one of the localized regions as a reference region, selecting at least another one of the localized regions as a comparison region, comparing a thermal response at the comparison region to a thermal response at the reference region due to the heating, and determining whether the object has a defect based on the comparison. There is also provided a corresponding system for detecting defects in an object.

20 Claims, 7 Drawing Sheets

(56) References Cited

U.S. PATENT DOCUMENTS

| | | |
|---|---|---|
| 2005/0147287 A1* | 7/2005 | Sakai .............. G01N 21/9501 382/141 |
| 2005/0214956 A1 | 9/2005 | Li et al. |
| 2006/0191622 A1 | 8/2006 | Ritter et al. |
| 2007/0047796 A1 | 3/2007 | Anantharaman |
| 2008/0111078 A1 | 5/2008 | Sun |
| 2008/0212072 A1 | 9/2008 | Piriou et al. |
| 2011/0249700 A1 | 10/2011 | Nakagawa et al. |

OTHER PUBLICATIONS

Vavilov et al., "Some Novel Approaches to Thermal Tomography of CFRP Composites," Quebec, Canada, Jul. 27-30, 2010, pp. 1-8.

Janke et al., "Composite Heat Damage Assessment," Proceedings: Conference on Characterization and NDE of Heat Damage in Graphite Eposy Composites, NTIAC, 1993, pp. 76-96.

Schlichting et al., "Flying Laser Spot Thermography for the Fast Detection of Surface Breaking Cracks," 18th World Conference on Nondestructive Testing, Session 42, Apr. 16-20, 2012, pp. 1-7.

Spicer et al., "Time-Resolved Infrared Radiometry of Multilayer Organic Coatings Using surface and Subsurface Heating," vol. 1467, Thermosense XIII, 1991, pp. 311-321.

Search Report issued by the Intellectual Property Office of Singapore for Singapore Patent Application No. 10201501913V, Sep. 25, 2017, pp. 1-3.

Written Opinion issued by the Intellectual Property Office of Singapore for Singapore Patent Application No. 10201501913V, Sep. 25, 2017, pp. 1-4.

Tewary et al., "Detection of Subsurface Defects using Active Infrared Thermography," 14th Asia Pacific Conference on Non-Destructive Testing, Nov. 30, 2013, pp. 1-6.

* cited by examiner

METHOD OF DETECTING DEFECTS IN AN OBJECT BASED ON ACTIVE THERMOGRAPHY AND A SYSTEM THEREOF

CROSS-REFERENCE TO RELATED APPLICATION

This application claims the benefit of priority of Singapore Patent Application No. 10201400586U, filed 12 Mar. 2014, the contents of which being hereby incorporated by reference in its entirety for all purposes.

TECHNICAL FIELD

The present invention generally relates to a method of detecting defects in an object based on active thermography and a system thereof, and more particularly, to a method and system capable of detecting low-contrast defects.

BACKGROUND

Thermography is an imaging technique based on infrared emission by an object at a particular temperature (grey body radiation). Thermography may include passive thermography or active thermography. Active thermography involves applying a stimulus to a target to cause the target to heat or cool in such a way as to allow characteristics of the target to be observed when viewed by thermal imagery. Active thermography plays a crucial role as a non-destructive technique (NDT) in many industries, especially in aerospace. Electromagnetic excitation is the most commonly used way of exciting the sample among thermographic techniques.

Thermography may also be classified as point imaging thermography, line imaging thermography, area imaging thermography and three-dimensional (3D) imaging thermography (tomography). Area or 3D imaging thermography may also be classified as one-sided or two-sided thermography. Active area imaging thermography may include a detector such as an infrared camera, a heating source as well as image processing software. For example, in a conventional one-sided optically excited thermography system, a flash lamp may be used as a source of electromagnetic radiation to illuminate a surface of a sample. An infrared camera is used to record the temperature evolution of the sample surface. The source and the detector are arranged on the same side in relation to the sample in the one-sided optically excited thermography. The camera and the flash lamp may be coupled to a computer. The computer may be configured to acquire data from the camera as well as configured to control the camera and flash lamp.

As another example, in a conventional two-sided optically excited thermography system, an infrared radiator or heating lamp may be used as a source of electromagnetic radiation to illuminate a sample. The infrared camera is arranged at the side (of the sample) opposite the radiator to record the temperature evolution. The source and the detector may be arranged on opposite sides in relation to the sample in the two-sided optically excited thermography. The camera may also be coupled to a computer.

The lamp radiator may be a tungsten filament lamp with broad spectral response but in general, alternative sources with spectral components from UV to microwave may also be utilized. This technique has been particularly successful in finding delaminations in Fiber Reinforced Plastics (FRP). The thermo-physical properties of such defects display a high contrast to the fibers and matrix of FRP. Such substantial contrasts allow the lateral conduction in the FRP to be disregarded and heat propagation within the sample be treated as a one-dimensional (1D) problem, making it possible to extract depth information from the thermography data. However, 1D model may only be valid if 3D diffusion can be ignored. For this to happen, one or several of the following criteria should be satisfied:

- The surface heating is uniform, so that there are no lateral gradients.
- The contrast in thermo-physical parameters between defect and sound regions of the sample is high enough to create temperature gradients much larger in comparison with deviation from one dimensional (1D) solution.
- The detection is performed shortly after the heat source is switched off, so that heat diffusion is minimal. Similarly this criterion can be defined if the location of the defect is close to the surface.

Another conventional approach is based on laser heating. In this approach, the heating may be performed in a non-uniform manner. Through such non-uniform heating, it is possible to detect defects that strongly affect lateral heat flow, like cracks. One of the recent examples is the flying laser spot thermography system. The interaction of laser with the surface is monitored continuously using an IR camera. When the laser spot is in the vicinity of a crack, the higher thermal resistivity of the crack leads to a reduced cooling and thus to a higher maximal temperature. Eventually, it gives rise to the thermal crack signature. By differentiation of the temperature profiles in different direction, the crack orientation can be reconstructed.

Few thermography methods based on laser are also employed for material properties evaluation. For example, in Time Resolved Infrared Radiometry (TRIR), the heating with a laser is used to determine thickness of the coating or the presence of delaminations. The same TRIR set-up may be used for detection of delaminations under the coating, which behave as disbonded material.

In the field of aerospace, different techniques have been applied for cracks and delaminations detection. Not restricting to active thermography, these techniques include x-ray examination, dye-penetrant, ultrasound, eddy-currents, etc., and discussion on the disadvantages has been carried out. Different methods in different set-up and orientation specifically targeting thermal imaging were also discussed.

A more recent discussion in the NDT industry involves the possibility of manipulating the shape of the source intensity with a constant output which clearly relates to forced diffusion thermographic instrument. Similar concept was also disclosed which uses the line-scanning method to heat and measure the sample with a photothermal test camera while the system design also allows manipulation of the laser beam shape. The contribution of ideas over the years prompted the introduction of algorithm calculation to enhance the capability of such systems. However, they only mention about the detection of high contrast defects such as cracks and delaminations, but none was found to include the detection of low-contrast defect such as minor heat damage.

There are several limitations of the conventional active thermography based on flash lamps, which limit its application only to the defects with high contrast in thermophysical parameters in relation to base material under inspection:

- It is too challenging to achieve uniform illumination of the material, which introduces lateral temperature gradients that will dominate the IR image.
- Even if the uniformity of illumination can be achieved, it is practically impossible to avoid variation of the light absorption at the surface, which will depend on material composition, surface structure and finishing and presence of surface contamination.

Even after the flash is applied, the glow from the lamp stays strong for several seconds and is reflected from the sample into the camera. This makes it impossible to use the thermography at early stages of thermal transition.

Application in ambient condition causes cooling of the surface through convection, which contributes significantly after 10 seconds of observation.

Some of the limitations of the thermography based on single laser are listed below:

It requires scanning of the single beam, which restricts the analysis to a relatively small area of the sample that can be examined in a reasonably short time.

Single laser approach makes it difficult to compare two different spots within the area of interest. The reason for this is that the analysis of one spot inevitably leads to the temperature increase in the whole part under investigation. Hence, the initial temperature condition for each consecutive spot is different. This issue can be ignored for high-contrast defects, like disbonds and cracks, but it will be detrimental for low-contrast defects, like incipient heat damage.

A need therefore exists to provide a method of detecting defects in an object based on active thermography and a system thereof, which seek to overcome, or at least ameliorate, one or more of the deficiencies of the conventional art mentioned above. It is against this background that the present invention has been developed.

SUMMARY

According to a first aspect of the present invention, there is provided a method of detecting defects in an object based on active thermography, the method comprising:

heating a surface of the object at a plurality of localized regions thereof;

selecting at least one of the localized regions as a reference region;

selecting at least another one of the localized regions as a comparison region;

comparing a thermal response at the comparison region to a thermal response at the reference region due to said heating; and determining whether the object has a defect based on the comparison.

In an embodiment, said comparing comprises computing a first value based a change in temperature detected at the comparison region and a change in temperature detected at the reference region due to said heating, and whether the object has a defect is determined based on the first value.

Preferably, the first value is computed based on a ratio of the change in temperature detected at the comparison region and the change in temperature detected at the reference region due to said heating.

Preferably, said determining whether the object has a defect comprises determining whether the first value is within a tolerance range from a predetermined value, and wherein the object is determined to have a defect if the first value is outside of the tolerance range.

Preferably, the predetermined value is 1.

Preferably, the tolerance range is about ±0.005 to ±0.015 from the predetermined value.

In a further embodiment, the method further comprises computing a second value based on a heat input at the comparison region and a heat input at the reference region due to said heating.

Preferably, the second value is computed based on a ratio of the heat input at the comparison region and the heat input at the reference region due to said heating.

Preferably, the method further comprises computing a third value based on the first value and the second value, wherein said determining whether the object has a defect comprises determining whether the third value is within a tolerance range from a predetermined value, and wherein the object is determined to have a defect if the third value is outside of the tolerance range.

Preferably, the third value is computed based on a ratio of the first value and the second value.

Preferably, the predetermined value is 1.

Preferably, the tolerance range is about ±0.005 to ±0.015 from the predetermined value.

Preferably, the plurality of localized regions is a plurality of spots on the surface of the object.

According to a second aspect of the present invention, there is provided a system for detecting defects in an object based on active thermography, the system comprising:

one or more heat sources configured for heating a surface of the object at a plurality of localized regions thereof;

a selection module configured to select at least one of the localized regions as a reference region and select at least another one of the localized regions as a comparison region;

a comparison module configured to compare a thermal response at the comparison region to a thermal response at the reference region due to said heating; and a decision module configure to determine whether the object has a defect based on the comparison by the comparison module.

In an embodiment, the comparison module is configured to compute a first value based a change in temperature detected at the comparison region and a change in temperature detected at the reference region due to said heating, and whether the object has a defect is determined based on the first value.

In a further embodiment, the comparison module is further configured to compute a second value based on a heat input at the comparison region and a heat input at the reference region due to said heating.

Preferably, the comparison module is further configured to compute a third value based on the first value and the second value, wherein the decision module is configured to determine whether the object has a defect by determining whether the third value is within a tolerance range from a predetermined value, and wherein the object is determined to have a defect when the third value is outside of the tolerance range.

Preferably, the predetermined value is 1 and the tolerance range is about ±0.005 to ±0.015 from the predetermined value.

In an embodiment, the heat source is configured to heat the surface at one side of the object at a plurality of localized regions thereof.

In another embodiment, the system comprises a plurality of heat sources configure for heating the surface of the object at a plurality of sides thereof.

According to a third aspect of the present invention, there is provided a computer program product, embodied in a computer-readable storage medium, comprising instructions executable by a computer processor to perform the method of detecting defects in an object based on active thermography according to the first aspect of the present invention.

BRIEF DESCRIPTION OF THE DRAWINGS

Embodiments of the present invention will be better understood and readily apparent to one of ordinary skill in the art from the following written description, by way of example only, and in conjunction with the drawings, in which.

DETAILED DESCRIPTION

Embodiments of the present invention provide a method of detecting defects in an object based on active thermography, and a system thereof. By way of examples only and without limitation, the object/structure to be examined or inspected for defects may be Fiber Reinforced Plastics (FRP), plastics, metals and metal alloys, or coatings. Active thermography involves applying a stimulus to a target to cause the target to heat or cool in such a way as to allow characteristics of the target to be observed when viewed by thermal imagery. Active thermography plays a crucial role as a non-destructive technique (NDT) to examine/inspect objects in many industries such as in building diagnostics and aerospace. As discussed in the background of the present invention, although conventional methods or techniques may be able to detect high-contrast defects, they do not include the detection of low-contrast defects such as minor heat damage, e.g., incipient heat damage. In contrast, embodiments of the present invention advantageously provide a method and a system capable detecting low-contrast defects in an object, and various embodiments will now be described below.

According to embodiments of the present invention, it was observed/recognized that uniform heating of a surface of an object is either impractical or not achievable in active thermography. Therefore, rather than attempting to control uniformity in the heating of a surface, the non-uniformity in the heating is controlled or addressed. In this regard, embodiments of the present invention advantageously direct heat to a surface of an object at multiple localized regions thereof, and the characteristics (temperature responses) at different localized regions of the surface are compared to determine whether the object being inspected has a defect. In an embodiment, at least one of the localized regions is selected as a reference region and at least another one of the localized regions is selected as a comparison region, and the temperature responses at the comparison region and the reference region are compared to determine whether the object has a defect. This approach or technique has been found to be able to successfully detect low-contrast defects (and thus also high-contrast defects) in an object, and will be demonstrated later according to example embodiments of the present invention.

Figure 1A:
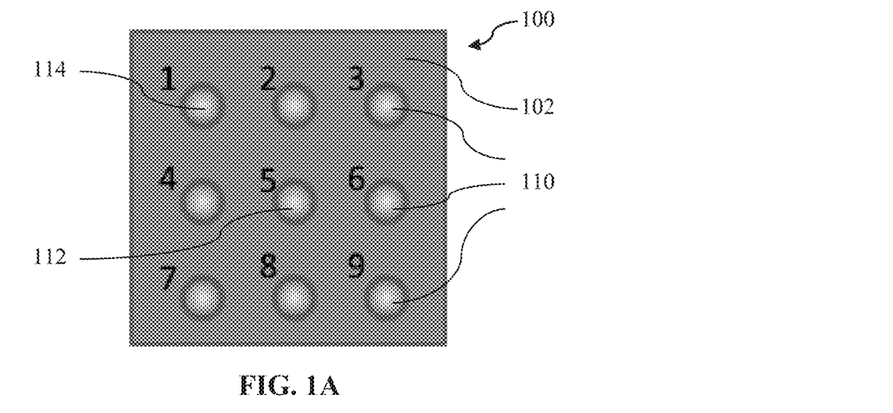
FIGS. 1A to 1C depict schematic drawings of a surface of an object heated/illuminated by one or more heat sources according to various embodiments of the present invention.

FIG. 1A depicts a schematic drawing of a surface 102 of an object heated/illuminated by one or more heat sources (not shown) according to an embodiment of the present invention. As shown, the surface 102 is heated at multiple localized regions 110 in the form of an array of spots, which may thus be referred to as multi-spot heating 100. It will be appreciated to a person skilled in the art that the present invention is not limited to the number of spots and their arrangement as shown in FIG. 1A. It will also be appreciated to a person skilled in the art that the surface 102 of the object to be inspected does not need to be flat and may be of any other shapes as appropriate such as a curved surface. In various embodiments, the array of spots 110 may be generated by a structured heating source such as multiple laser sources or one laser source by splitting the one laser beam into different laser beams using either free standing optics or diffractive optics, or fiber bundle.

Figure 1B:
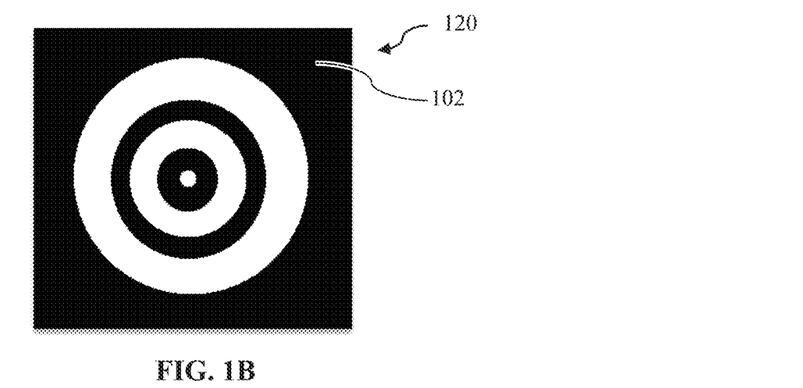
Figure 1C:
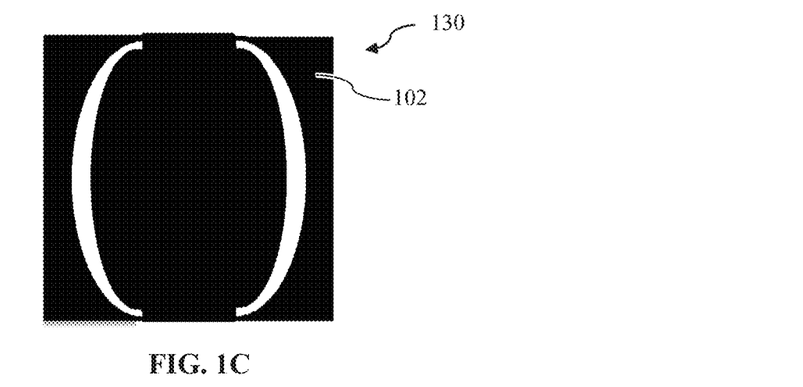

Although preferred, it will be appreciated that the present invention is not limited to multi-spot heating 100 as illustrated in FIG. 1A and may be other types or configurations of heating as long as multiple localized regions 110 of the object surface 102 is heated/illuminated, such as concentric heating 120 as shown in FIG. 1B or crescent heating (heat focusing) 130 as shown in FIG. 1C.

Figure 2:
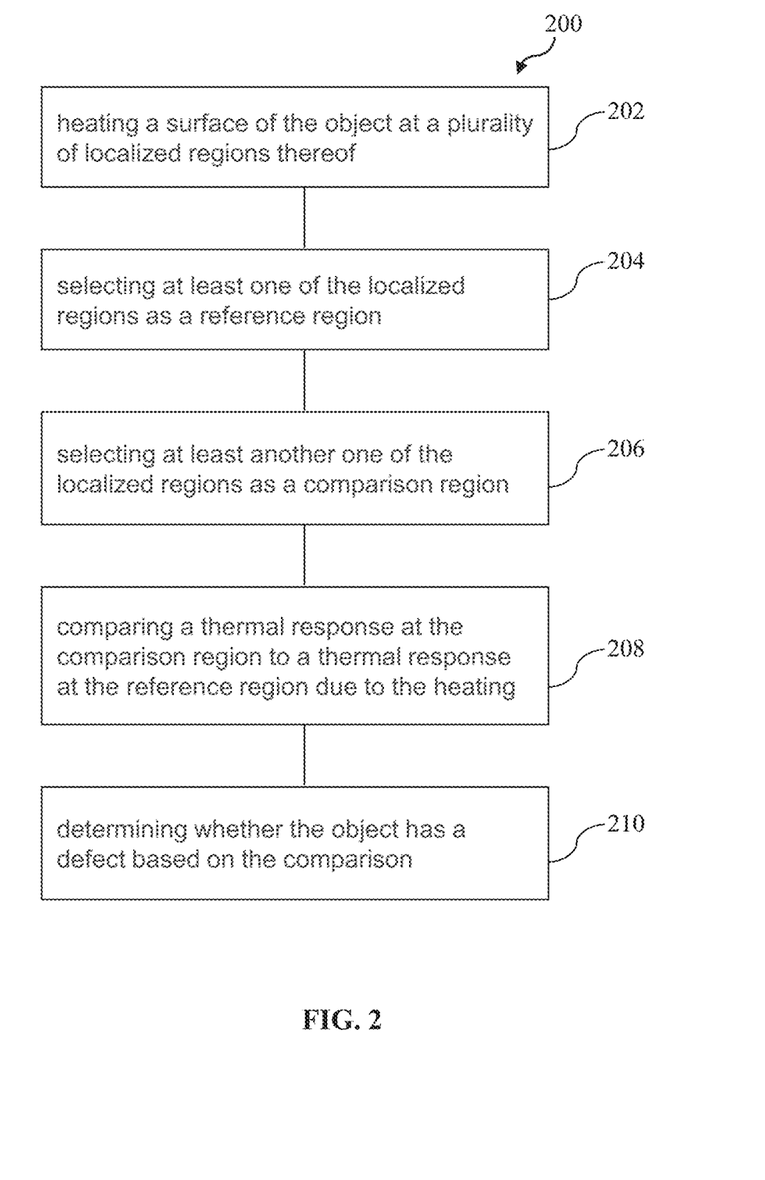
FIG. 2 depicts a broad overview of a method of detecting defects in an object based on active thermography according to an embodiment of the present invention.

FIG. 2 depicts a broad overview of a method 200 of detecting defects in an object according to an embodiment of the present invention. The method 200 comprises a step 202 of heating a surface 102 of the object at a plurality of localized regions 110 thereof (for example, an array of spots as illustrated in FIG. 1A), a step 204 of selecting at least one of the localized regions 110 as a reference region (for example and without limitation, the spot denoted with reference number 112 in FIG. 1A), a step 206 of selecting at least another one of the localized regions 110 as a comparison region (for example and without limitation, the spot denoted with reference number 114 in FIG. 1A), a step 208 of comparing a thermal response (preferably temperature response) at the comparison region 114 to a thermal response (preferably temperature response) at the reference region 112 due to the heating, and a step 210 of determining whether the object has a defect based on the comparison in step 208.

As will be demonstrated later according to example embodiments of the present invention, the method 200 has been found to significantly improve the sensitivity of the defect detection and thus capable of successfully detecting low-contrast defects in objects.

In an embodiment, the step 208 of comparing comprises computing a first value based a change in temperature detected at the comparison region 114 and a change in temperature detected at the reference region 112 due to the heating at such regions. Preferably, the first value is computed based on a ratio of the change in the temperature detected at the comparison region 114 and the change in temperature detected at the reference region 112 due to the heating at such regions. Thereafter, whether the object has a defect is determined based on the first value. In particular, it is determined whether the first value is within a tolerance range from a predetermined value, and the object is determined to have a defect if the first value computed is outside of the tolerance range.

In this regard, ideally, whether a defect exists is simply whether the first value equals the predetermined value. However, it will be appreciated to a person skilled in the art that due to various factors in practice, such as inevitable measurement errors, environmental factors and measurement equipment stability, the first value computed would generally not be exactly equal to the predetermined value even if there is no defect, but will be substantially equal to the predetermined value (i.e., within a tolerance range from the predetermined value). Particular care has to be taken in relation to control of absorbed laser power. This includes laser source stability (e.g., achievable below 1%) and control of absorption coefficient (mainly due to reflection variation based on fiber orientation). Therefore, it will be appreciated to a person skilled in the art that there is generally no fixed values for the tolerance range as it depends on various factors such as the material of the object under inspection, the layout/configuration of the object, and the desired size of the defects to be detected (i.e., detection sensitivity). Thus, the tolerance range may be determined or established as appropriate. However, it will be appreciated that the method 200 is advantageously able to minimize the effects of such factors and thus able to produce more accurate results and capable of detecting low-contrast defects.

In a preferred embodiment, the predetermined value is 1, which will be explained in example embodiments later. By way of example only and without limitation, the tolerance range may be about ±0.01. In various embodiments, the range may be increased or decreased where necessary or appropriate, such as ±0.005 to ±0.015 from the predetermined value.

Thus, the method 200 advantageously heats and measures the thermal response of the surface 102 at multiple localized regions 110 simultaneously whereby at least one of the localized regions 110 is used as a reference and at least another one of the localized regions 110 is used for comparison to the reference. This has been found to significantly improve the sensitivity of the defect detection and enable the method 200 to successfully detect low-contrast defects.

The method 200 may also have the following advantages over conventional methods. For example, by increasing the number of localized regions or spots 110, the proportionally larger area can be investigated in comparison with conventional single laser heating. In addition, spatially separated spots will not affect each other at least within a period of time shorter than $L^2/2\alpha$, where L is the distance between spots and a is a thermal diffusivity of a material under investigation. Furthermore, in the multiple regions/areas approach, measurements in different areas are performed simultaneously, hence enabling referencing between different locations on the object and perform relative comparison of these areas.

According to an embodiment of the present invention, the heat input (i.e., power density absorbed or heat transfer rate) $(Q_i)$ in the respective localized region 110 is also taken into consideration to address the case where the size/dimension of the regions/areas may be different or even if they are suppose to be identical, it is not possible to achieve perfectly identical regions due to, for example, laser instability and/or variations in absorption. In this embodiment, the method 200 further comprises computing a second value in respect of the comparison region 114 based on a heat input at the comparison region 114 and a heat input at the reference region 112 due to the heating at such regions. Preferably, the second value is computed based on a ratio of the heat input at the comparison region 114 and the heat input at the reference region 112 due to the heating at such regions.

In this embodiment, the method 200 further comprises computing a third value based on the first value and the second value. Preferably, the third value is computed based on a ratio of the first value and the second value. Thereafter, in order to determine whether the object has a defect, it is determined whether the third value is within a tolerance range from a predetermined value, and the object is determined to have a defect if the third value is outside of the tolerance range. Preferably, the predetermined value is 1, which will also be explained in example embodiments later. As explained hereinbefore, the tolerance range is to account for various factors affecting the measurement results in practice and thus may be adjusted accordingly. For example, in various embodiments, the range may be increased depending on various factors such as the level of degradation of the sample desired to be detected. In an embodiment, the tolerance range from the predetermined value may be ±0.01. In various embodiments, the tolerance range may be ±0.005 to ±0.015 from the predetermined value.

This embodiment further improves the accuracy of the method 200 by taking into account the heat inputs in the respective localized regions 110, and thus advantageously allowing the method 200 to detect even lower contrast defects.

Figure 3:
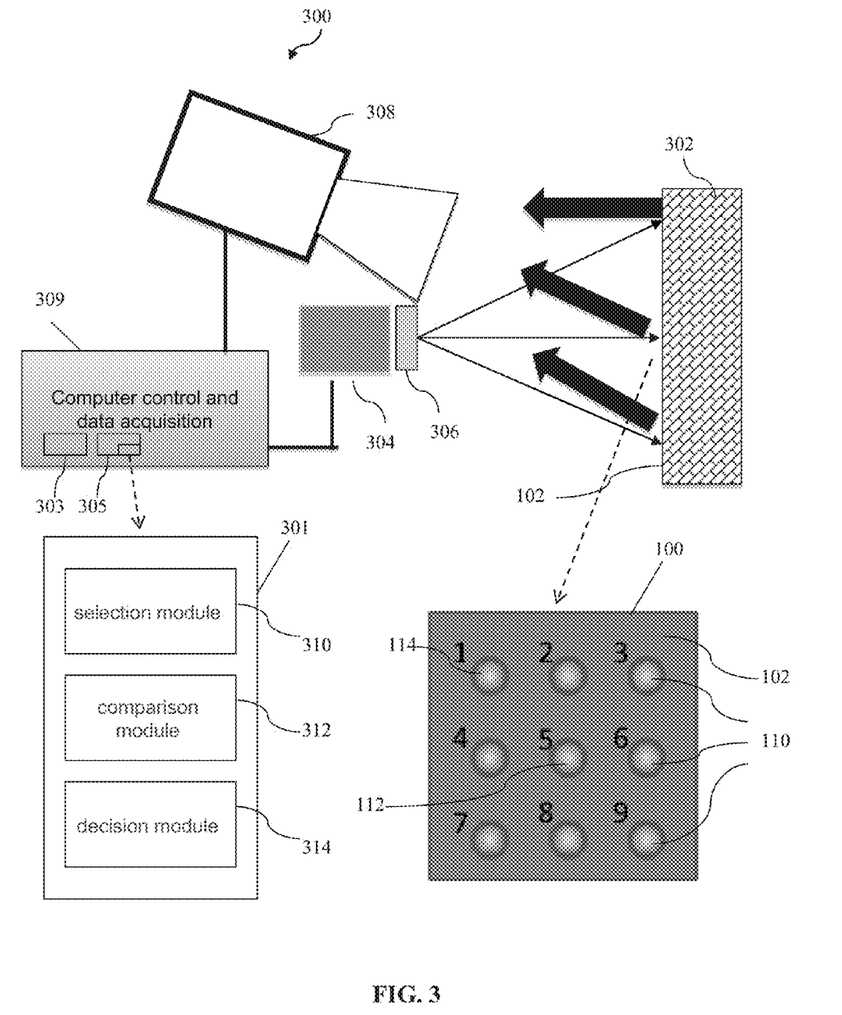
FIG. 3 depicts a schematic drawing of a system for detecting defects in an object based on active thermography according to an embodiment of the present invention.

According to an embodiment, there is provided a system 300 for detecting defects in an object based on active thermography as illustrated in FIG. 3 corresponding to the method 200 as illustrated in FIG. 2. The system 300 comprises a heat source (e.g., laser) 304 with a beam splitter/shaper 306 configured for heating a surface 102 of the object 302 at a plurality of localized regions 110 thereof, a monitor/detector (e.g., an infrared sensor or camera) 308 for monitoring/detecting the characteristics (e.g., thermal response) of the surface 102 of the object due to the heating, a selection module 310 configured to select at least one of the localized regions 110 as a reference region 112 and select at least another one of the localized regions 110 as a comparison region 114, a comparison module 312 configured to compare a thermal response at the comparison region 114 to a thermal response at the reference region 112 due to the heating at such regions based on the information/data received from the detector 308, and a decision module 314 configured to determine whether the object has a defect based on the comparison by the comparison module 312. It will be appreciated to a person skilled in the art that the system 300 is not limited to being configured as a one-sided thermography as shown in FIG. 3 and may have any other type of configuration as appropriate such as a two-sided thermography.

It will be appreciated to a person skilled in the art that the selection module 310, the comparison module 312, and the decision module 314 may be realized or put into effect by computer code or program 301 (instructions executable by a computer processor 303 of a computing device/system (e.g., computer control and data acquisition system) 309. The computer program 301 may be stored in any computer readable storage medium 305 such as hard disk drive, magnetic or optical disks, memory chips, or other storage devices.

The heat source 304 with beam splitter/shaper 306 may be any structured heating source configured to be able to heat or illuminate the surface 102 at a plurality of localized regions 110 thereof. For example, the plurality of localized regions 110 may be generated by multiple laser sources each emitting a laser beam onto a respective one of the localized regions 110 or by one laser source coupled with a structure (e.g., beam splitter/shaper 306) for splitting/shaping the one laser beam emitted into multiple laser beams onto the localized regions 110.

According to an embodiment of the present invention, there is provided a computer program product 301, embodied in a computer-readable storage medium 305, comprising instructions executable by a computer processor 303 to perform the method 200 of detecting defects in an object based on active thermography as described above with reference to FIG. 2.

Some portions of the description are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate.

In addition, the present specification also implicitly discloses a computer program or software/functional module, in that it would be apparent to the person skilled in the art that the individual steps of the methods described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer program when loaded and executed on such a general-purpose computer effectively results in an apparatus that implements the steps of the methods described herein.

The software or functional modules described herein may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, various lengths, sizes and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

For a better understanding, an exemplary implementation of the method 200 of detecting defects in an object will now be described based on the multi-spot heating 100 as shown in FIG. 1A according to an example embodiment of the present invention. In particular, as shown in FIG. 1A, a surface 102 of the object is heated/illuminated by an array of equivalent laser spots 110. After a sufficiently long period, the maximum temperature at any spot 110 on the surface 102 will depend only on Q, a, and k according to following equation:

$$\Delta T = \frac{Q \times a}{k} \quad (1)$$

where ΔT is the temperature increase (or change) after the laser is switched on, Q is the power density absorbed (or heat transfer rate) within a laser spot, a is the radius of the laser spot, and k is the thermal conductivity.

In the example embodiment, one of the spots 110 is selected as a reference (i.e., reference spot or region). For example and without limitation, the reference spot 112 can be chosen at a location with known damage level (e.g., highest or lowest). In another embodiment, the reference spot may be at a special calibrated sample independent of the object/structure under investigation. Then, a comparison/normalization procedure is performed based on the following equation:

$$(T_i - T_0)/(T_{ref} - T_0) = K_i \quad (2)$$

where $T_0$ is the room temperature, $T_i$ is the temperature at a selected spot (i.e., comparison spot or region), $T_{ref}$ is the temperature at the reference spot, and K is a value (first value) obtained as a result of the comparison based on Equation (2).

Based on Equation (2), for undamaged object/material, K=1, while for damaged object/material, K≠1 (i.e., the predetermined value is 1). As explained hereinbefore, due to various factors, the object may be considered as having no defects if the value of K obtained is within a tolerance range from the predetermined value, such as a range of ±0.01.

Assuming that perfectly identical spots are not achievable either due to laser instability or variations in absorption, then the ratio of power density absorbed ($Q_i$) at a selected spot are also taken into consideration based on the following equation:

$$Q_i/Q_{ref} = M \quad (3)$$

where $Q_i$ is the power density absorbed at the selected/comparison spot, $Q_{ref}$ is the power density absorbed at the reference spot, and M is a value (second value) obtained based on Equation (3).

In the example embodiment, for undamaged material, K/M=1, while for the damaged material, K/M≠1. In particular, a third value is obtained as a ratio of K (first value) and M (second value) and the third value is compared against a predetermined value of 1 to determine whether the object has a defect. As explained hereinbefore, due to various factors, the object may be considered as having no defects if the third value obtained is within a tolerance range from the predetermined value, such as a range of ±0.01.

In order to demonstrate the defects detection results of the method according to the example embodiment, a simulation was conducted where the temperature responses for three spots are considered with an initial temperature of $T_0$=24 C.°. At a first spot, the power density absorbed is Q and the material properties are at 100% of expected value (i.e., no damages or defects). At a second spot, the power density absorbed is doubled (2Q) and the material properties are unchanged at 100%. In a third spot, the power density absorbed is at the same level as in the first spot (Q), but the material's effective thermal conductivity is changed due to a low-contrast damage or defect by 5% (i.e., 95% of original value).

Figure 4:
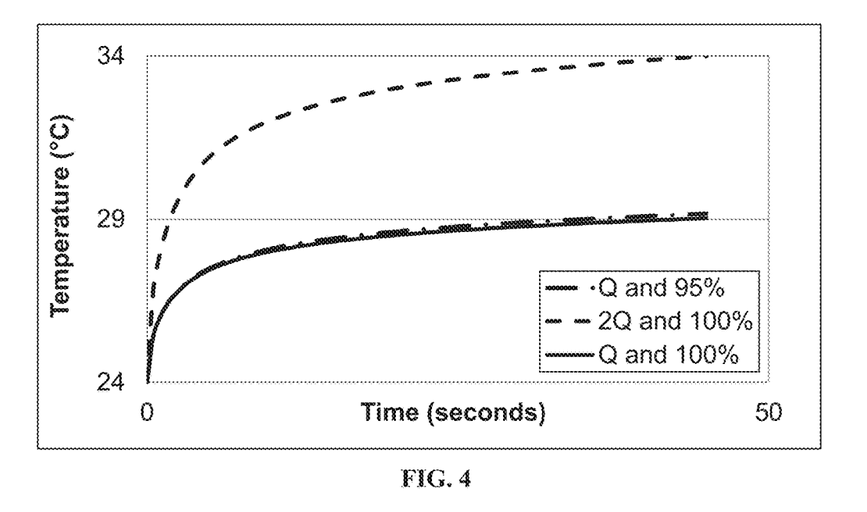
FIG. 4 depicts a graph showing the simulated temperature responses for three regions/spots.

FIG. 4 depicts a graph showing the simulated temperature responses (temperature in ° C.) for the above-mentioned three spots. As shown in the graph of FIG. 4, the doubling of the power density absorbed causes the temperature at the second spot to also double, while at the third spot although there exists a low-contrast defect, only a very marginal temperature increase can be observed in comparison with first and second spots without defects. Therefore, it is difficult to detect such a low-contrast defect without implementing the defect detection method according to embodiments of the present invention.

Figure 5:
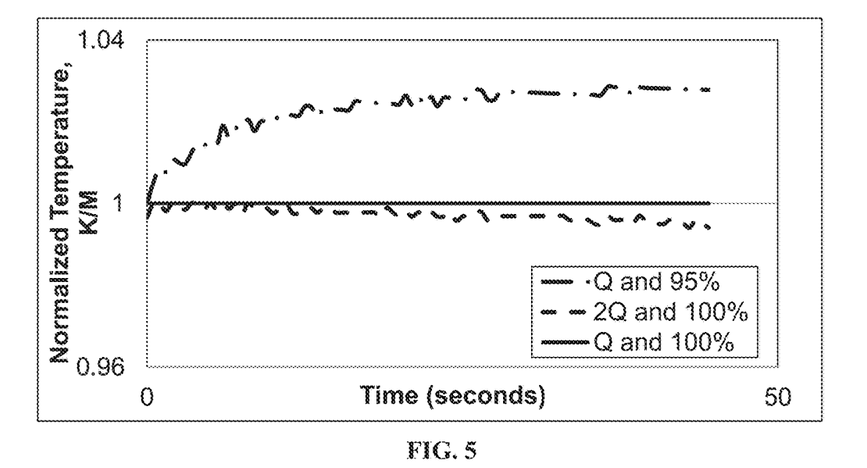
FIG. 5 depicts a graph showing the normalized temperature responses for the same three spots as FIG. 4 obtained based the method according to an embodiment of the present invention.

In stark contrast, FIG. 5 depicts a graph showing the temperature responses (normalized temperature (i.e., third value, K/M)) for the same three spots obtained by implementing the method according to the example embodiment based on Equations 2 and 3. As can be observed from FIG. 5, when the power density absorbed is increased at the second spot, the normalized temperature (i.e., K/M) obtained at the second spot is still substantially the same as the normalized temperature obtained at the first spot. However, it can be observed from the graph that if the effective thermal conductivity of the sample are changed by just 5% (low-contrast defect) in the example, the measured value (K/M) is 3% larger for the third spot (having low-contrast defect) in comparison with the first and second spots (having no defects). Therefore, this clearly demonstrates that the method according to embodiments of the present invention is advantageously able to detect low-contrast defects.

Figure 6:
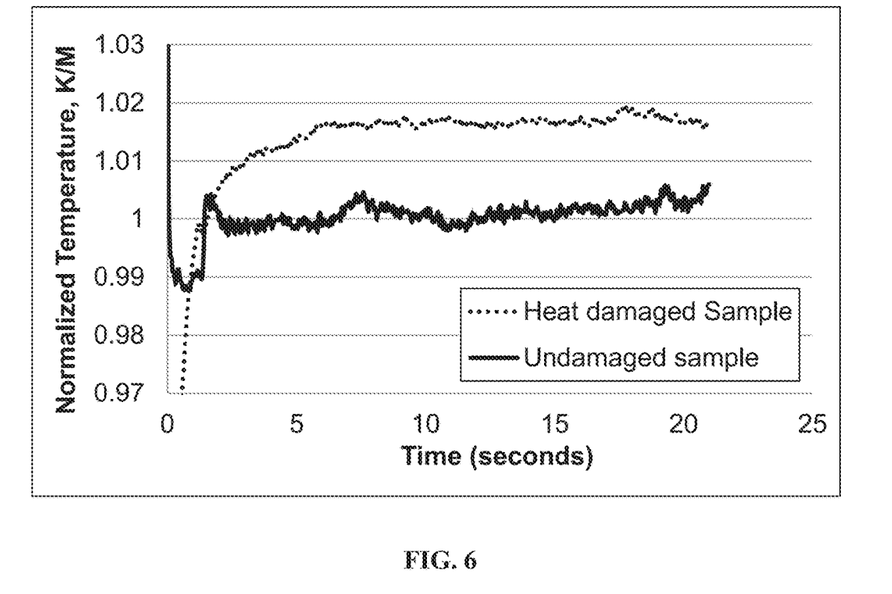
FIG. 6 depicts a graph showing the averaged measurement results (normalized temperature responses (K/M)) for a heat damaged sample and an undamaged sample according to an example embodiment of the present invention.

In order to verify the results of the above-described simulation, an experiment was performed for a heat damaged sample (low-contrast defect) and an undamaged sample (no defects). On each sample, the measurement was performed five times with five different laser power levels. FIG. 6 depicts a graph showing the averaged values of the measurements for each of the two samples. From FIG. 6, it can be observed that the values of K/M have increased by approximately 2% for the damaged sample compared to the undamaged sample. Based on mechanical measurements, it was found that the damaged sample have shown only 80% of the strength measured for undamaged sample. Therefore, this demonstrate the ability of the present method to detect low-contrast defects and also the importance of detecting low-contrast defects since even such low-contrast defects may significantly affect the strength of the material/object.

It will be appreciated to a person skilled in the art that since the method according to embodiments are able to detect low-contrast defects, the method is also able to detect high-contrast defects.

Figure 7:
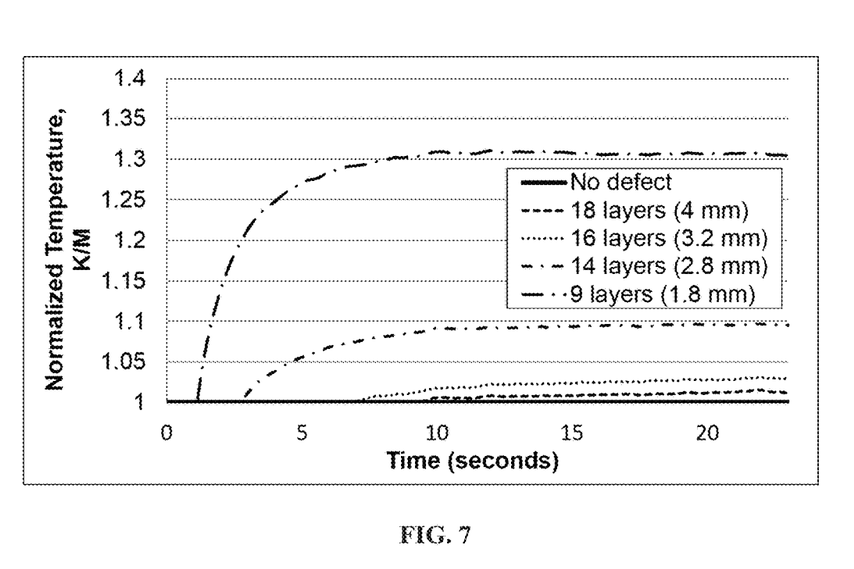
FIG. 7 depicts a graph showing the measurement results (K/M) of high thermal conductivity carbon-fiber-reinforced polymer (CFRP) samples with delaminations at various depths according to an example embodiment of the present invention.

As a further illustration, FIG. 7 shows the measurement results (K/M) of high thermal conductivity carbon-fiber-reinforced polymer (CFRP) samples with delaminations at various depths by applying the present method according to the example embodiment of the present invention. As shown in FIG. 7A, the delaminations at 1.8 mm, 2.8 mm, 3.2 mm and 4 mm below the surface resulted in the K/M values of about 1.31, 1.10, 1.03 and 1.01, respectively. Therefore, this demonstrates that the present method is able to successfully detect low-contrast defects at various depths of an object.

Therefore, it can be seen that the present technique of comparing different spots is advantageously simple and effective in detecting low-contrast defects (as well as high-contrast defects) in objects.

Figure 8A:
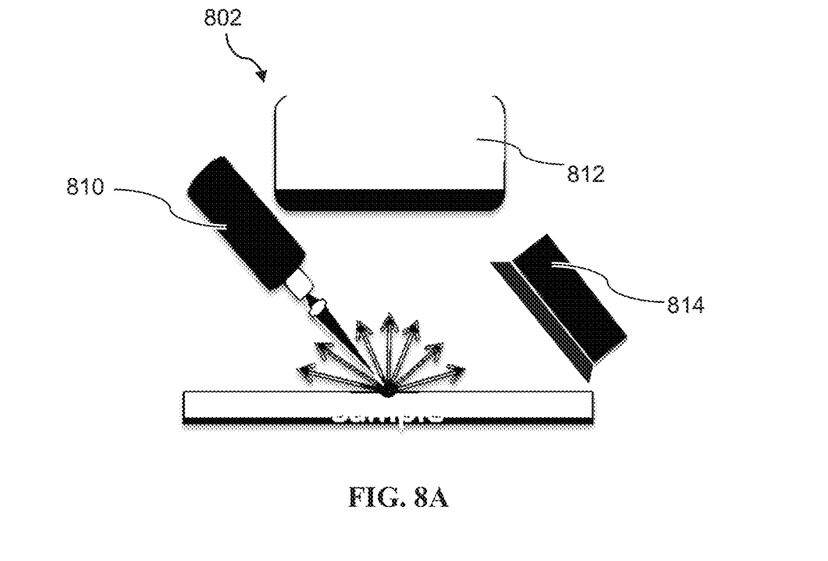
FIGS. 8A and 8B depict schematic drawings of a system for detecting defects in an object based on active thermography according to another embodiment of the present invention.
Figure 8B:
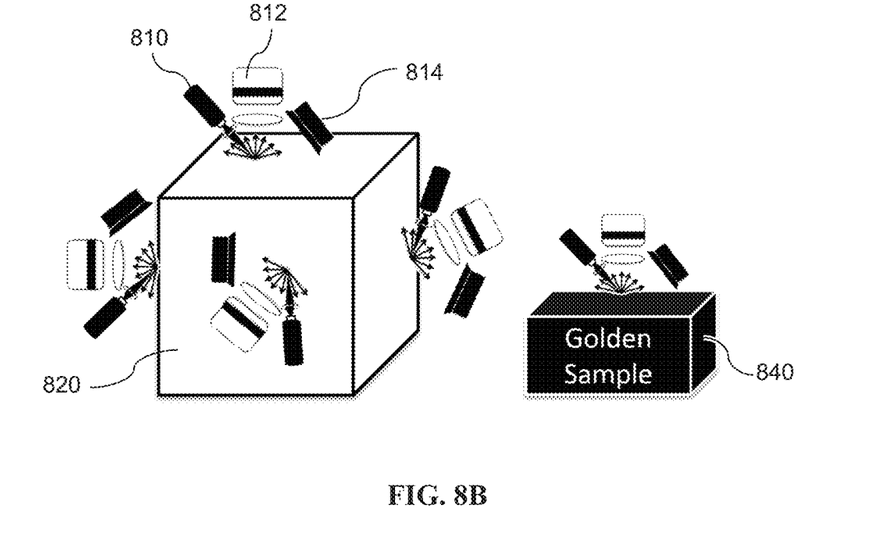

FIG. 8A depicts a schematic diagram of a system for detecting defects in an object based on active thermography according to an embodiment of the present invention. In particular, instead an array illumination as shown in FIG. 3, a combined head 802 comprising a heat source (e.g., laser) 810 and a sensor (e.g., infrared (IR)) 812 is implemented as shown in FIG. 8A by way of example only. Additionally, a monitoring system 814 is implemented for assessing reflection and scattering loss at the same position. This has been found to drastically reduce the uncertainty in measurements. For example, by distributing the combined laser and IR sensor head 802 around the structure of interest (object) 820 as illustrated in FIG. 8B, a qualitative and quantitative analysis can be performed for thermal response in a similar manner as described hereinbefore.

In an embodiment, for more stable results, all heads can be initially applied to the same standard substrate 840, so that the variation in Q can be compensated. Subsequently, one of the heads can stay on the standard samples, while the other heads may evaluate the thermal response of the sample 820. Therefore, advantageously, this technique can be implemented not only on the flat or curved surface, but also for a variety of complex shapes.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of detecting defects in an object based on active thermography, the method comprising:
   heating a surface of the object at a plurality of localized regions thereof, each of the plurality of localized regions being heated for a period of time sufficient to reach thermal equilibrium;
   selecting at least one of the plurality of localized regions as a reference region;
   selecting at least another one of the plurality of localized regions as a comparison region;
   comparing a thermal response at the comparison region to a thermal response at the reference region due to said heating; and
   determining whether the object has a defect based on the comparison.

2. The method according to claim 1, wherein said comparing comprises computing a first value based a change in temperature detected at the comparison region and a change in temperature detected at the reference region due to said heating, and whether the object has a defect is determined based on the first value.

3. The method according to claim 2, wherein the first value is computed based on a ratio of the change in temperature detected at the comparison region and the change in temperature detected at the reference region due to said heating.

4. The method according to claim 3, wherein said determining whether the object has a defect comprises determining whether the first value is within a tolerance range from a predetermined value, and wherein the object is determined to have a defect if the first value is outside of the tolerance range.

5. The method according to claim 4, wherein the predetermined value is 1.

6. The method according to claim 1, further comprises computing a second value based on a heat input at the comparison region and a heat input at the reference region due to said heating.

7. The method according to claim 6, wherein the second value is computed based on a ratio of the heat input at the comparison region and the heat input at the reference region due to said heating.

8. The method according to claim 6, further comprises computing a third value based on the first value and the second value, wherein said determining whether the object has a defect comprises determining whether the third value is within a tolerance range from a predetermined value, and wherein the object is determined to have a defect if the third value is outside of the tolerance range.

9. The method according to claim 8, wherein the third value is computed based on a ratio of the first value and the second value.

10. The method according to claim 8, wherein the predetermined value is 1.

11. The method according to claim 10, wherein the tolerance range is about ±0.005 to ±0.015 from the predetermined value.

12. The method according to claim 1, wherein the plurality of localized regions is a plurality of spots on the surface of the object.

13. A system for detecting defects in an object based on active thermography, the system comprising:
   one or more heat sources configured to heat a surface of the object at a plurality of localized regions thereof such that each of the plurality of localized regions is heated for a period of time sufficient to reach thermal equilibrium;
   a selection module configured to select at least one of the plurality of localized regions as a reference region and select at least another one of the plurality of localized regions as a comparison region;
   a comparison module configured to compare a thermal response at the comparison region to a thermal response at the reference region due to said heating; and
   a decision module configure to determine whether the object has a defect based on the comparison by the comparison module.

14. The system according to claim 13, wherein the comparison module is configured to compute a first value based a change in temperature detected at the comparison region and a change in temperature detected at the reference region due to said heating, and whether the object has a defect is determined based on the first value.

15. The system according to claim 14, wherein the comparison module is further configured to compute a second value based on a heat input at the comparison region and a heat input at the reference region due to said heating.

16. The system according to claim 15, wherein the comparison module is further configured to compute a third value based on the first value and the second value, wherein the decision module is configured to determine whether the object has a defect by determining whether the third value is within a tolerance range from a predetermined value, and wherein the object is determined to have a defect when the third value is outside of the tolerance range.

17. The system according to claim 16, wherein the predetermined value is 1 and the tolerance range is about ±0.003 to ±0.015 from the predetermined value.

18. The system according to claim 13, wherein the heat source is configured to heat the surface at one side of the object at a plurality of localized regions thereof.

19. The system according to claim 13, comprising a plurality of heat sources configure for heating the surface of the object at a plurality of sides thereof.

20. A computer program product, embodied in a computer-readable storage medium, comprising instructions executable by a computer processor to perform a method of detecting defects in an object based on active thermography, the method comprising:

heating a surface of the object at a plurality of localized regions thereof, each of the plurality of localized regions being heated for a period of time sufficient to reach thermal equilibrium;

selecting at least one of the plurality of localized regions as a reference region;

selecting at least another one of the plurality of localized regions as a comparison region;

comparing a thermal response at the comparison region to a thermal response at the reference region due to said heating; and determining whether the object has a defect based on the comparison.

* * * * *